United States Patent
Welsch et al.

(10) Patent No.: US 9,422,669 B2
(45) Date of Patent: *Aug. 23, 2016

(54) PROCESS FOR PREPARING STABLE DISPERSIONS OF STARCH PARTICLES

(71) Applicant: DOW GLOBAL TECHNOLOGIES LLC, Midland, MI (US)

(72) Inventors: Gregory W. Welsch, Midland, MI (US); Brian J. Ninness, Midland, MI (US); Michael D. Read, Midland, MI (US); Timothy J. Young, Bay City, MI (US); Michal E. Matteucci, Midland, MI (US); David E. Hammond, Saginaw, MI (US); Liang Hong, Midland, MI (US); Donald K. Ervick, Jr., Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/090,127

(22) Filed: Nov. 26, 2013

(65) Prior Publication Data

US 2014/0083329 A1 Mar. 27, 2014

Related U.S. Application Data

(63) Continuation of application No. 13/153,854, filed on Jun. 6, 2011.

(60) Provisional application No. 61/352,209, filed on Jun. 7, 2010.

(51) Int. Cl.
| | |
|---|---|
| *D21H 19/12* | (2006.01) |
| *C08B 30/02* | (2006.01) |
| *C08B 30/06* | (2006.01) |
| *C08B 30/08* | (2006.01) |
| *C08J 3/05* | (2006.01) |
| *C08J 3/12* | (2006.01) |
| *C08L 3/02* | (2006.01) |
| *C09D 103/02* | (2006.01) |
| *C09J 103/02* | (2006.01) |
| *C12P 19/04* | (2006.01) |
| *D21H 19/54* | (2006.01) |
| *D21H 17/28* | (2006.01) |

(52) U.S. Cl.
CPC ............... *D21H 19/12* (2013.01); *C08B 30/02* (2013.01); *C08B 30/06* (2013.01); *C08B 30/08* (2013.01); *C08J 3/05* (2013.01); *C08J 3/12* (2013.01); *C08L 3/02* (2013.01); *C09D 103/02* (2013.01); *C09J 103/02* (2013.01); *C12P 19/04* (2013.01); *D21H 19/54* (2013.01); *C08J 2303/02* (2013.01); *D21H 17/28* (2013.01); *Y10T 428/2982* (2015.01); *Y10T 428/31971* (2015.04)

(58) Field of Classification Search
CPC ....... D21H 19/12; D21H 17/28; D21H 19/54; C08B 30/02; C08B 30/06; C08B 30/08; C08J 3/05; C08J 3/12; C08J 2303/02; C08L 3/02; C09D 103/02; C09J 103/02; Y10T 428/2982; Y10T 428/31971
USPC .......... 428/402; 427/391, 393.5, 395; 524/47; 536/106; 106/206.1
See application file for complete search history.

(56) References Cited

U.S. PATENT DOCUMENTS

| | | | |
|---|---|---|---|
| 6,252,121 B1 | 6/2001 | Argyropoulos et al. | |
| 6,677,386 B1 | 1/2004 | Giezen et al. | |
| 6,737,099 B2 | 5/2004 | Guraya et al. | |
| 6,825,252 B2 * | 11/2004 | Helbling et al. | 524/47 |
| 7,160,420 B2 * | 1/2007 | Helbling et al. | 162/175 |
| 7,285,586 B2 * | 10/2007 | Helbling et al. | 524/47 |
| 2009/0005552 A1 * | 1/2009 | Hassan et al. | 536/102 |
| 2009/0005553 A1 * | 1/2009 | Hassan et al. | 536/102 |

FOREIGN PATENT DOCUMENTS

| | | | |
|---|---|---|---|
| DE | 10251599 | | 3/2004 |
| EP | 1176255 | * | 1/2002 |

OTHER PUBLICATIONS

International Search Report and Written Opinion for related PCT Application PCT/US2011/001019, mailed Dec. 12, 2011 (9 pgs).

* cited by examiner

*Primary Examiner* — Leszek Kiliman
(74) *Attorney, Agent, or Firm* — Brooks, Cameron & Huebsch, PLLC

(57) ABSTRACT

In one or more embodiments, the present disclosure provides for a process for preparing a dispersion of starch particles in an aqueous liquid. In one or more embodiments, the process includes introducing a feed starch and the aqueous liquid into a rotor stator mixer, maintaining the feed starch and the aqueous liquid in the rotor stator mixer at a temperature ranging from a gelation temperature to less than a solubilization temperature, and shearing the feed starch into starch particles with the rotor stator mixer to form the dispersion of starch particles in the aqueous liquid. In one or more embodiments, the starch particles produced by this process have an average particle size diameter of no larger than 2 micrometers and the dispersion has 20 to 65 weight percent of the starch particles based on a total weight of the dispersion.

14 Claims, 3 Drawing Sheets

PROCESS FOR PREPARING STABLE DISPERSIONS OF STARCH PARTICLES

This application is a Continuation of U.S. application Ser. No. 13/153,854, filed Jun. 6, 2011, which claims the benefit to U.S. Provisional Application Ser. No. 61/352,209, filed Jun. 7, 2010, the entire contents of which are incorporated herein by reference in its entirety.

FIELD OF DISCLOSURE

Embodiments of the present disclosure are directed toward a process for preparing starch; more specifically, embodiments are directed toward a process for preparing stable dispersions of starch particles.

BACKGROUND

Synthetic latexes are important components in the binder systems of coatings used in the paper coating industry. Synthetic latexes used in these applications typically have a high solid content (48-58 weight percent solid) and a low viscosity that allows for ease of handling, and good runnability and stability in the paper coating process. Synthetic latexes also allow for excellent particle size control, viscoelasticity control (e.g., glass transition temperature (Tg) and modulus), and dry and wet strength of the resulting coatings.

In addition to synthetic latexes, starch can also be useful in the binder systems of coatings used in the paper coating industry. For examples, starch has been used as a partial substitute for synthetic latexes in the binder systems of coatings used in the paper coating industry. Among its advantages, starch is a relatively low cost material having excellent water holding and thickening properties while providing stiffness, porosity and blocking resistance to the resulting coating. There are, however, limitations in the use of starch in these applications. These limitations include poor runnability during application and poor product performance of the coating compositions, especially as the level of latex substitution increases.

To overcome these challenges, it would be advantageous for paper coating applications, among others, to develop a starch product which can be made at a high solid content (45-65 weight percent) while maintaining a low viscosity of 2000 cP or less similar to synthetic latexes, and preferably with an average particle size diameter of no larger than 2 micrometers.

SUMMARY

One or more embodiments of the present disclosure include a process for preparing a stable dispersion of starch particles in an aqueous liquid. In one or more embodiments, the process includes introducing a feed starch and the aqueous liquid into a rotor stator mixer, maintaining the feed starch and the aqueous liquid in the rotor stator mixer at a temperature ranging from a gelation temperature to less than a solubilization temperature of the feed starch, and shearing the feed starch into starch particles with the rotor stator mixer to form the stable dispersion of starch particles in the aqueous liquid.

In one or more embodiments, shearing the feed starch into starch particles produces starch particles having an average particle size diameter of no larger than 2 micrometers. Other average particle size diameters for the starch particles are also possible. For example, in one or more embodiments shearing the feed starch into starch particles produces starch particles having an average particle size diameter of no larger than 1 micrometer. In another example, in one or more embodiments shearing the feed starch into starch particles produces starch particles having an average particle size diameter of 10 to 200 nanometers.

In one or more embodiments, shearing the feed starch into starch particles includes forming the dispersion having 20 to 65 weight percent of the starch particles based on a total weight of the dispersion. In one or more embodiments, shearing the feed starch into starch particles includes forming the dispersion having 35 to 55 weight percent of the starch particles based on a total weight of the dispersion. In one or more embodiments, shearing the feed starch into starch particles includes forming the dispersion having 45 to 55 weight percent of the starch particles based on a total weight of the dispersion. In one or more embodiments, shearing the feed starch into starch particles includes forming the dispersion having 48 to 55 weight percent of the starch particles based on a total weight of the dispersion.

In one or more embodiments, the starch particles are sheared in the absence of a cross-linker. In one or more embodiments, shearing the feed starch into starch particles is conducted in the absence of a surfactant and/or a cross-linker. In one or more embodiments, shearing the feed starch into starch particles is conducted in the presence of a surfactant and/or a cross-linker. In one or more embodiments, shearing the feed starch, in addition to producing starch particles, produces soluble starch having a starting molecular weight, where the soluble starch can be reduced from the starting molecular weight to an ending molecular weight that is less than the starting molecular weight. In one or more embodiments, reducing the soluble starch includes enzymatically reducing the soluble starch from the starting molecular weight to an ending molecular weight less than the starting molecular weight.

In one or more embodiments, the viscosity of the dispersion having 20 to 65 weight percent by weight of the starch particles, based on a total weight of the dispersion, is less than 10,000 cP after being at 25° C. for at least 24 hours, for example at 24 hours. In one or more embodiments, the process of the present disclosure also includes at least partially removing the aqueous liquid from the starch particles of the dispersion.

In one or more embodiments, the dispersion of starch particles prepared by the process of the present disclosure can be included in a binder composition, an adhesive composition and/or a coating composition. In one or more embodiments, the coating composition can be a paper coating composition, among other types of coating compositions. In one or more embodiments, the coating composition can be a filth forming composition. In one or more embodiments, the coating composition can be applied to one or more surfaces of a substrate. In one or more embodiments, the coating composition applied to one or more surfaces of the substrate can have at least a portion of the aqueous liquid removed, thereby forming a coating layer (e.g. a film), a binder layer or an adhesive layer associated with one or more surfaces of the substrate. In one or more embodiments, the coating layer, binder layer or the adhesive layer formed with the dispersion produced according to the present disclosure can be continuous, discontinuous, or combinations thereof. In one or more embodiments, removing at least a portion of the aqueous liquid can be removed via drying, centrifuge, freeze drying, filtration, absorption and combinations thereof. In one or more embodiments, an article can be formed with the coating composition, where the article can have a substrate having one or more surfaces, and one or more coating layers associated with one or more surfaces of the substrate, where the coating layer is derived from the coating composition.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DEFINITIONS

Figure 1:
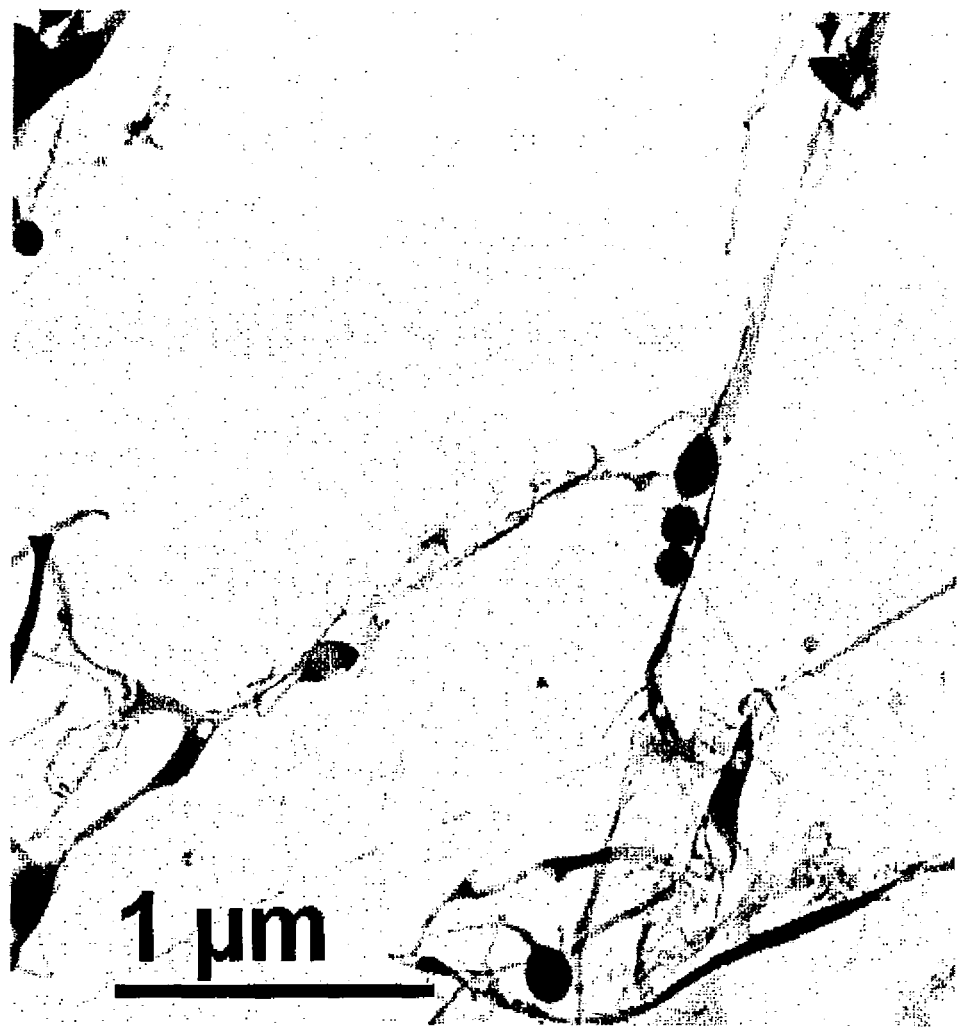
FIG. 1 provides a transmission electron microscopy (TEM) image of a soluble starch from a feed starch that has been "cooked" beyond the solubilization temperature but not gelled according to the present disclosure.

As used herein, the terms "a," "an," "the," "one or more," and "at least one" are used interchangeably and include plural referents unless the context clearly dictates otherwise.

Unless defined otherwise, all scientific and technical terms are understood to have the same meaning as commonly used in the art to which they pertain. For the purpose of the present disclosure, additional specific terms are defined throughout.

As used herein, "μm" is an abbreviation for micrometer.

As used herein, "° C." is an abbreviation for degree Celsius.

As used herein, "cP" is an abbreviation for Centipoise, a unit of measurement in the cgs system for viscosity.

The terms "comprises," "includes" and variations of these words do not have a limiting meaning where these terms appear in the description and claims. Thus, for example, a process that comprises "a" feed starch can be interpreted to mean a process that includes "one or more" feed starches. In addition, the term "comprising," which is synonymous with "including" or "containing," is inclusive, open-ended, and does not exclude additional unrecited elements or method steps.

As used herein, the term "and/or" means one, more than one, or all of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "feed starch" can include, a carbohydrate polymer composed of various ratios of amylose and amylopectin joined by glucosidic bonds and having and/or being in a crystalline or semi-crystalline state. The feed starch can be selected from a wide variety of sources including, but are not limited to, corn, potato, tapioca, rice, wheat, barley, and other grains and/or tubers (e.g., root or stem tubers), and of those may include waxy, native, unmodified native, and/or high amylose starches. Specific non-limiting examples include waxy corn starch (e.g., a high amylopectin starch) and dent starch, among others. The feed starch can also include "modified" feed starch which can include a modified starch (e.g., corn, potato, tapioca, among others) prepared by acetylation, chlorination, acid hydrolysis, enzymatic action, or other modification process. This "modified" feed starch can be purposefully modified in order to deliver other benefits such as carboxylated starches, hydroxyethylated starches, resistant starches, thermally oxidized starches, dextrin type, among others. In one or more embodiments, the feed starch can have a number of different properties and/or forms. These include, but are not limited to, a dry powder and/or an intermediate starch product such as a cake, and/or a slurry having moisture content in the range of equal or less than 80 weight percent, for example, in the range of from 35 to 80 weight percent; or in the alternative from 35 to 75 weight percent; or in the alternative from 35 to 65 weight percent. In one or more embodiments, the feed starch has discrete units having an average particle size diameter of about 15 to about 40 micrometer (μm); for example, from 15 to 35 μm; or in the alternative, from 15 to 30 μm; or in the alternative from 20 to 40 μm. Mixtures of two or more of the feed starch provided herein are also possible, and would be considered to be a "feed starch" as provided and discussed herein.

As used herein "dry" means no greater than about 8 to about 14 percent water by weight absorbed in and/or bound to a substance (e.g., the feed starch).

As used herein, the term "cross-linker" means a compound which attaches at least two chains of polymer molecules through carbon atoms by primary chemical bonds. In one or more embodiments, different categories of a cross-linker include, but are not limited to, Amino Resins (Urea Formaldehyde and Melamine Formaldehyde), Glyoxal Resins, and Metallic Ions (Zirconium complexes). If a cross-linker is employed with the dispersion of the present disclosure, the selection of the cross-linker can depend at least in part on the reactive groups available on the starch particles, the ingredients of the coating, binder and/or adhesive composition and/or the end use of the coated substrate. The term insolubilizer is also often used to define the function of crosslinking chemistry in conjunction with starch.

As used herein, the term "surfactant" means a compound that reduces surface tension when dissolved in water or water solutions, or that reduces interfacial tension between two liquids, or between a liquid and a solid.

Figure 2:
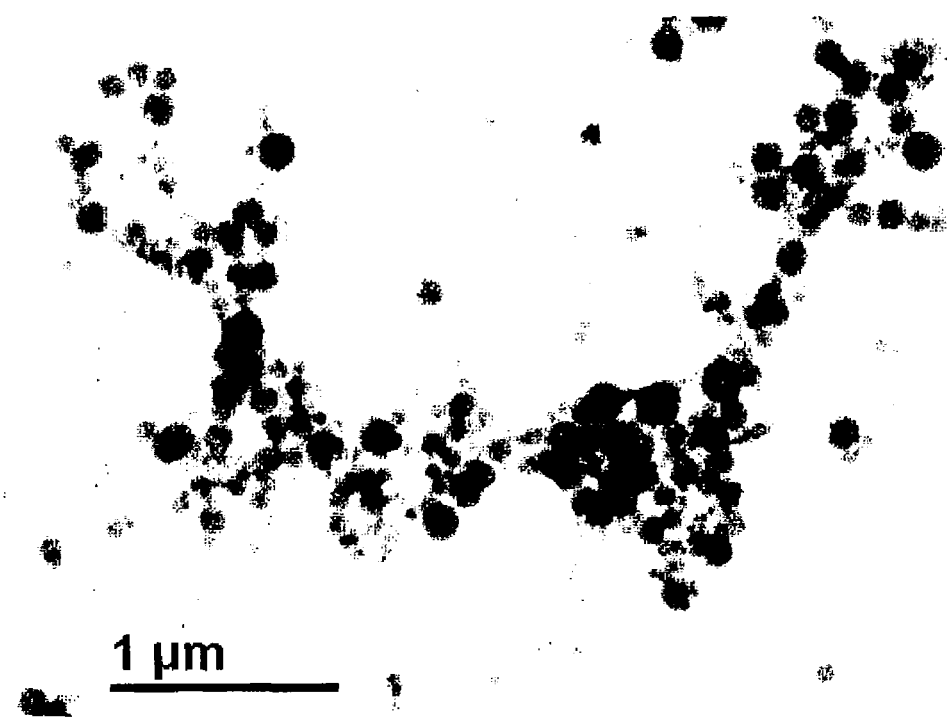
FIG. 2 provides a TEM image of a stable dispersion of starch particles in an aqueous liquid according to the present disclosure.

As used herein, the term "soluble starch" means a starch released and/or leached from the feed starch granule into the aqueous liquid while being heated to or at a temperature ranging from a gelation temperature to below a solubilization temperature of the feed starch, where the soluble starch is present in the aqueous phase between the starch particles of the present disclosure. In one embodiment, the soluble starch may be additionally characterized by being small enough so as not to scatter light in the visible spectrum (e.g., from about 380 or 400 nanometers to about 760 or 780 nanometers). FIG. 1 provides a transmission electron microscopy (TEM) image of soluble starch forming a network of starch molecules (e.g., the interconnected "spider web" like threads) without the presence of the starch particles of the present disclosure, which are shown in FIG. 2, as discussed herein.

As used herein, the term "dispersion" means a two-phase system where one phase consists of starch particles, as defined herein, dispersed throughout an aqueous liquid, as defined herein, which forms a continuous phase. For the present disclosure, starch particles can be dispersed in an aqueous liquid where the starch particles have an average particle size diameter of no larger than 2 micrometers.

As used herein, the term "aqueous liquid" includes water or a water solution that can include compounds (ionic or non-ionic) such as organic compounds, inorganic compounds, water soluble polymer, fats, oils, proteins, polysaccharides, salts, sugars, acids, alcohols, alkalis and gases that help to adjust and/or maintain a pH, a salinity, an electrical conductivity, dielectric constant, and/or a boiling point, among others.

Figure 3:
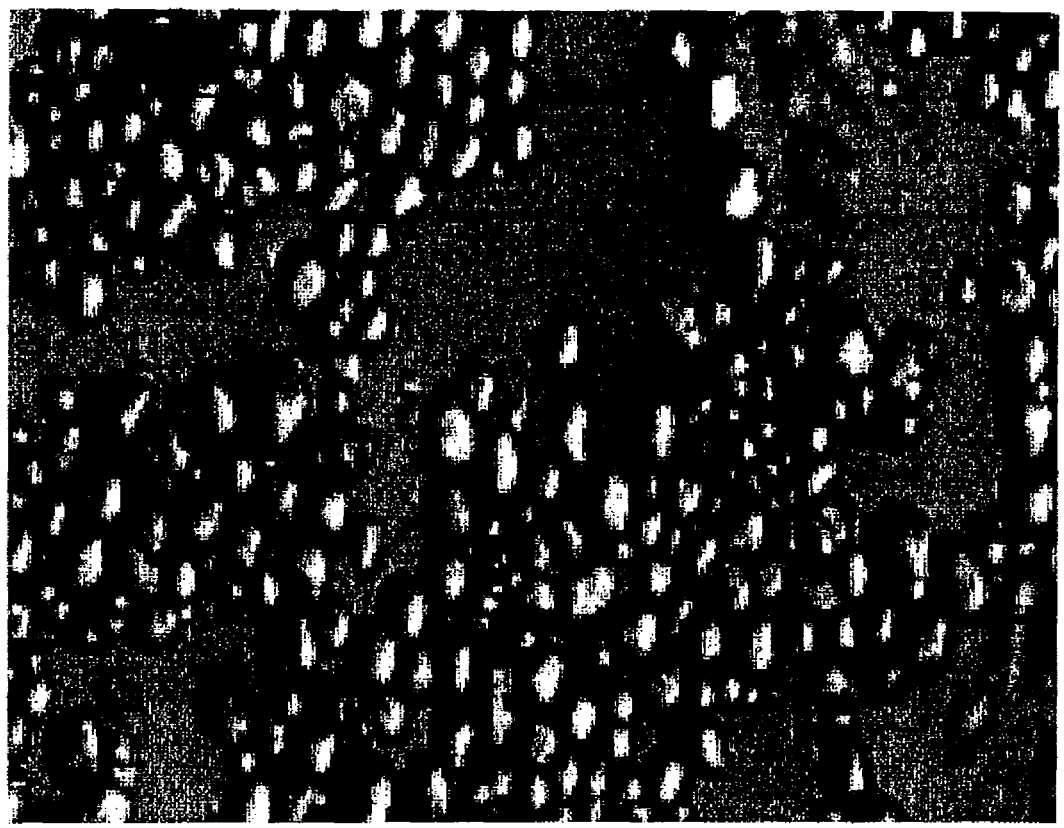
FIG. 3 provides an optical microscope image of starch granules formed from a feed starch in an aqueous liquid but kept below the gel temperature during shearing.

As used herein, the term "starch particles" refers to a discrete unit derived from the feed starch using the methodology of the present disclosure, where the discrete units have an amorphous structure and an average particle size diameter of no larger than 2 micrometers, where average particle size diameters of no larger than 1 micrometers or average particle size diameters of 10 to 200 nanometers are possible. FIG. 2 provides a TEM image of a stable dispersion of starch particles in an aqueous liquid according to the present disclosure, as is more fully discussed herein. The size and shape of the starch particles in FIG. 2 are in contrast to the optical microscope image of dispersed starch granules shown in FIG. 3, where the starch granules were formed by shearing a feed starch in a rotor stator mixer at a temperature below the gelation temperature of the feed starch.

As used herein, the term "stable" or "stability" means the ability and the duration of the starch particles of the present disclosure to remain as a dispersion in the aqueous liquid due to Brownian movement of the starch particles in the aqueous liquid, where any settling of the starch particles can be reversed by agitation. The stable dispersion of the starch particles of the present disclosure does not gel or "set-up" under the conditions of the dispersion given herein.

As used herein, the term "rotor stator mixer" refers to a high-shear mixing apparatus that disperses, or transports, the starch particles into the aqueous liquid, as provided herein, by mechanical agitation. In one or more embodiments, the rotor stator mixer includes at least one impeller or rotor, or a series of impellers and/or rotors, powered by a motor, e.g. an electric motor, and at least one stationary component (e.g., a stator) that creates a close clearance gap with the rotor so as to produce an extremely high shear zone for the material (e.g., the feed starch) as it exits the rotor. Factors such as the diameter of the rotor and its rotational speed (e.g. ramps and cycles), the design of the stator ring such as number and rows of teeth, their angle and the distance between the rotor and the stator (e.g., the clearance gap), the residence time and the number of rotor stator mixers used all effect the generation of the dispersion of the starch particles in the aqueous liquid. Examples of such high-shear mixing apparatus include, but are not limited to, batch high shear mixers, inline high shear mixers, ultra high shear inline mixers, and grinding mills. In one embodiment, embodiments of the rotor stator mixers, however, exclude extruders.

As used herein, the term "gelation temperature" refers to a temperature and a pressure at which the crystalline structure of the feed starch transforms at least partially from its crystalline and/or semi-crystalline state to combine with the aqueous liquid to produce a viscous jellylike product.

As used herein, the term "solubilization temperature" refers to a temperature and a pressure at which the feed starch has no remaining crystallinity and becomes a uniformly dispersed mixture at the molecular level in and with the aqueous liquid.

As used herein, the terms "swell," "swelling," and/or "swollen," refer to an increase in the volume of the feed starch due at least in part to a loss in crystallinity of the initial structure of the feed starch and the absorption of an aqueous liquid into the resulting amorphous structure of the feed starch.

As used herein, the term "ambient conditions" refers to a temperature of around 25° C. (e.g., 25° C.) and a pressure of 101.325 kiloPascal (kPa) (1 atmosphere).

As used herein, the term "specific mechanical energy (SME)" is defined as the total input of mechanical energy per unit mass of material flowing through the rotor stator mixer of the present disclosure. The units of SME presented herein are in Joules per gram (J/g).

As used herein, the term "redispersible" is defined as a powder formulation that readily disperses and hydrates into an aqueous liquid. The polymer powders are typically produced by subjecting an aqueous dispersion of the polymer to a drying operation in which its volatile components are evaporated, for example by means of spray drying or freeze drying. The evaporation of the aqueous dispersion medium may be accompanied by irreversible aggregation of the polymer particles of the aqueous dispersion with one another, to form secondary particles. The formation of secondary particles results in poorer redispersibility, which is generally accompanied by poorer performance properties of the powder. Therefore, good redispersibility in water is one of the most important properties of the water-redispersible polymer powders.

DETAILED DESCRIPTION

Embodiments of the present disclosure describe the use of a rotor stator mixer for producing a dispersion of starch particles in an aqueous liquid. In one or more embodiments, the starch particles of the present disclosure are formed from a feed starch. In one or more embodiments, the feed starch and the aqueous liquid are heated to a temperature ranging from a gelation temperature to below a solubilization temperature of the feed starch. At this temperature, the structure of the feed starch swells as it loses its crystalline structure and absorbs at least a portion of the aqueous liquid to achieve an amorphous structure. The feed starch in its swollen state undergoes shearing to allow for the production of the starch particles of the dispersion. Dispersions of the present disclosure can have improved shelf-stability, high solid content and low viscosity, as discussed herein.

In one or more embodiments, the starch particles produced according to the present disclosure are believed to retain the amorphous structure of the swollen feed starch from which they are produced. The starch particles with their amorphous structure also can retain a discrete state in the dispersion of the present disclosure at ambient conditions, as provided herein. In contrast, it is believed that if the solubilization temperature of the feed starch were to be achieved and/or exceeded (e.g., the starch has been "cooked" and is referred to as "cooked starch") and sufficient water is available, the amorphous structure of the feed starch would be destroyed to such an extent that starch particles having the structure and size could not be formed according to the processes of the present disclosure.

In one or more embodiments, the sizes of the starch particles of the present embodiments are orders of magnitude smaller than the feed starch. This reduction in size greatly increases the number of starch particles per unit volume for various uses, as discussed herein, as compared to the use of the feed starch alone. In one or more embodiments, even though the number of starch particles per unit volume can result in a high solid content, as discussed herein, the viscosity of the dispersion remains surprisingly low at ambient conditions. In one or more embodiments, it is believed that this surprisingly low viscosity can be at least partially attributed to reduced interactions between the starch particles of the present disclosure, as compared to a situation where the feed starch was fully solubilized before forming the dispersion.

In one or more embodiments, the high solid content/low viscosity dispersion of the present disclosure can be achieved without chemical modification of the starch particles. In one or more embodiments, it is also believed that the size reduction of the starch particles may lead to enhanced stability and better properties of coatings formed from coating compositions that include the dispersion of the present disclosure. As discussed more fully herein, coating compositions that include the dispersion of the present disclosure can be used in applications such as coating compositions, adhesive compositions, and/or binder compositions, among others as discussed herein.

In one or more embodiments, the process of the present disclosure includes introducing the feed starch and the aqueous liquid into the rotor stator mixer. The feed starch can be introduced into the rotor stator mixer as provided by the manufacturer (e.g., a dry powder, a cake, and/or a slurry) and/or can be pre-wetted prior to introduction into the rotor stator mixer. In one or more embodiments, the amount of water included with the feed starch, regardless of its source, is counted as a part of the aqueous liquid in the determination of the amount of aqueous liquid in the rotor stator mixer. In one or more embodiments, the weight of water is excluded, however, from the calculation of the dry weight of the feed starch.

In one or more embodiments, a suitable quantity of the aqueous liquid can be introduced with the feed starch to ensure both absorption of the aqueous liquid into the feed starch and to allow for swelling of the feed starch and for the dispersion of the present disclosure to be formed. In addition, during the initial shearing process of the feed starch and the aqueous liquid there is also believed to be a need to have a sufficient solids content (e.g., feed starch) of the starting mixture to facilitate shearing of the swollen feed starch into a stable dispersion of the starch particles of the present disclosure. An example of this is illustrated in the Examples provided herein.

In one or more embodiments, the amount of aqueous liquid introduced with the feed starch into the rotor stator mixer can be from 40 weight percent (wt. %) to 55 wt. %, based on the weight of the aqueous liquid and the feed starch. All individual values and subranges from 40 wt. % to 55 wt. %, based on the weight of the aqueous liquid and the feed starch are included herein and disclosed herein; for example, the aqueous liquid introduced with the feed starch into the rotor stator mixer can be from a lower limit of 40 wt. %, 45 wt., or 50 wt. % to an upper limit of 55 wt. %, or 50 wt. % (where it is possible that the lower limit and the upper limit are both a value of 50 wt. %). For example, the amount of aqueous liquid introduced with the feed starch into the rotor stator mixer can be from 40 wt. % to 55 wt. %, from 40 wt. % to 50 wt. %, from 45 wt. % to 55 wt. %, from 45 wt. % to 50 wt. %, or from 50 wt. % to 55 wt. %.

In one or more embodiments, the rotor stator mixer can supply and/or remove heat to achieve and/or maintain the temperature of the feed starch and the aqueous liquid from the gelation temperature to below the solubilization temperature of the feed starch. For example, the rotor stator mixer can include a heating/cooling jacket that can be used to control the temperature of the feed starch and the aqueous liquid in it large bulk phase inside the rotor stator mixer. In one or more embodiments, heating and/or cooling can be supplied through steam and/or water having a sufficient temperature difference with the bulk phase of the feed starch and the aqueous liquid to cause heating and/or cooling as desired. The action of the rotor stator may also contribute heat energy to the feed starch and the aqueous liquid, which may have to be removed by the heating/cooling jacket of the rotor stator mixer.

In one or more embodiments, the temperature at which the feed starch is processed allows for the feed starch to swell so as to achieve a proper size and hydration for shearing to the starch particles, which in turn have a size appropriate for creating Brownian motion sufficient to keep them suspended in the dispersion. In one or more embodiments, maintaining the feed starch and the aqueous liquid in a temperature range from the gelation temperature to less than the solubilization temperature of the feed starch causes the feed starch to lose its crystalline structure and promotes the absorption of the aqueous liquid. As the crystalline structure is lost and the feed starch absorbs the aqueous liquid it begins to swell. The feed starch, however, does not solubilize in the aqueous liquid (e.g., is not allowed to solubilize in the aqueous liquid) as the temperature of the feed starch in the aqueous liquid does not achieve or exceed the solubilization temperature of the feed starch.

As appreciated, the exact temperature ranges (e.g., from the gelation temperature to less than the solubilization temperature) will be a function of the feed starch selected for processing according to the present disclosure. By way of example, when waxy corn is used as the feed starch the temperature can range from about 68° C. (the gelation temperature of waxy corn at atmospheric pressure) to about 82° C. (the solubilization temperature of waxy corn at atmospheric pressure), where these temperature values are given as examples with the knowledge that they may be different for different waxy corn grades from different producers and/or based on seasonal changes in the starch raw material.

It is appreciated that the gelation temperature and the solubilization temperature of the feed starch can also be affected by the pressure at which the dispersion process takes place in the rotor stator mixer. Pressure such as, for example, 101 kPa to 3447 kPa, may be applied to facilitate processing. In other embodiments, the pressure can be from 101 kPa to 1379 kPa, or from 101 kPa to 689 kPa. Such exemplary pressure can be suitable for rotor stator mixers that operate as a continuous process, a semi-continuous process and/or a batch process.

In addition to swelling as it absorbs the aqueous liquid, the feed starch in the rotor stator mixer is also exposed to a shear force of sufficient magnitude so as to allow for the formation of the starch particles of the dispersion. In one or more embodiments, the rotor stator mixer can impart specific mechanical energy (SME) sufficient to form the dispersion of the present disclosure. For example, the rotor stator mixer can impart SME in a range of 100 Joules per gram (J/g) of the components that lead to the starch dispersion to 2000 J/g during the shearing of the feed starch into starch particles. In another example, the rotor stator mixer can impart SME in a range of 100 (J/g) of the components that lead to the starch dispersion to 1000 J/g during the shearing of the feed starch into starch particles.

In one or more embodiments, the SME can also have other value ranges, which may depend upon the rheology of the aqueous liquid, the feed starch contained in the rotor stator mixer and/or the type and/or configuration of the rotor stator mixer used in the process. Examples of such ranges can also include, but are not limited to, all individual values and subranges from 100 J/g to 2000 J/g; for example, the SME value can be from a lower limit of 100 J/g, 150 J/g, or 200 J/g to an upper limit of 2000 J/g, 1000 J/g, 875 J/g, or 750 J/g. For example, the SME value can be from 100 J/g to 2000 J/g, 100 J/g to 1000 J/g, from 100 J/g to 875 J/g, from 150 J/g to 750 J/g or from 200 J/g to 750 J/g, among others.

In one or more embodiments, the SME provided by the rotor stator mixer can add heat to the bulk phase of the feed starch, the aqueous liquid and the starch particles present therein. Specifically, this energy can be added in an around the shear zone of the rotor stator mixer (the area in and directly around the actual rotor stator and/or mixer structure), which can cause a local temperature increase. The residence time of the feed starch, the aqueous liquid and the starch particles in this area, however, is very short. In addition, the feed starch, the aqueous liquid and the starch particles having been heated in the shear zone are then almost immediately mixed back with the large bulk phase of the aqueous liquid, which help to control the temperature in the range provided herein. This is not the case with other systems, e.g., extruders and/or jet cookers.

In one or more embodiments, geometries of the rotor and/or the stator can be tuned to achieve a desired SME and/or shear rates for the rotor stator mixer. The operational speed (e.g., the rotations per minute) of the rotor may also be adjusted to create the appropriate amount of shear for the desired particle size reduction. In one or more embodiments, it is also possible to have a stator ring that can be engaged and disengaged relative the rotor. This allows for disengaging the stator from the rotor as the temperature of the feed starch, aqueous liquid and starch particles produced during the process begins to approach, but not exceed the solubilization temperature of the feed starch. In one or more embodiments, it is also possible to adjust a residence time values for the feed starch in the rotor stator mixer by recirculation of the product through the mixing zone of the rotor stator mixer. In one or more embodiments, the rotor stator mixer can also include baffling and/or an independently driven distributive mixing impeller (e.g. turbine or propeller) to ensure adequate mixing and turnover within the rotor stator mixer.

In one or more embodiments, shear from the rotor stator mixer breaks the feed starch in its swollen state into the discrete units that become the starch particles. As discussed herein, shearing the feed starch produces starch particles having an average particle size diameter greater than 0 micrometers but no larger than 2 micrometers (i.e., no larger than 2 micrometers), where sizes of greater than 0 micrometers but no larger than 1 micrometers (i.e., no larger than 1 micrometers) and/or 10 to 200 nanometers are possible.

In one or more embodiments, the average particle size diameter of the starch particles can be measured using transmission electron microscopy. Light scattering techniques are not effective for determining the average particle size diameter of the starch particles as the materials appear to loosely agglomerate, giving inaccurate results. In one or more embodiments, determining the number-weighted average particle size diameter can be accomplished by measuring the diameter of a predetermined number of starch particles and then determining the mathematical mean of the diameters of the measured particles to arrive at the number-weighted average particle size diameter.

The high solid content of the dispersion formed according to the present disclosure advantageously is, in various embodiments, at least 20 wt. % of the starch particles based on a total weight of the dispersion, at least 35 wt. % of the starch particles based on a total weight of the dispersion, at least 45 wt. % of the starch particles based on a total weight of the dispersion, or at least 48 wt. % of the starch particles based on a total weight of the dispersion, and advantageously is at most 65 wt. % of the starch particles based on a total weight of the dispersion, or at most 55 wt. % of the starch particles based on a total weight of the dispersion. Combinations of the upper and the lower limits are possible. In one or more embodiments, the high solid content is from 20 wt. % to 65 wt. % of the starch particles based on a total weight of the dispersion. In one or more embodiments, the high solid content is from 35 wt. % to 65 wt. % of the starch particles based on a total weight of the dispersion. In one or more embodiments, the high solid content is from 45 wt. % to 55 wt. % of the starch particles based on a total weight of the dispersion. In one or more embodiments, the high solid content is from 48 wt. % to 55 wt. % of the starch particles based on a total weight of the dispersion.

The dispersions of the present disclosure, in addition to having a high solid content (e.g. the starch particles), can also have a very low viscosity relative to conventional starch solutions at the same high solid content. In one or more embodiments, even with a high solid contents of the dispersion being from an upper to a lower limit as provided herein (based on a total weight of the dispersion) the dispersion can also have a viscosity of 2000 cP or less, or 1000 cP or less as measured at ambient conditions. So, for example, with a high solid contents of the dispersion being from 20 wt. % to 65 wt. % based on a total weight of the dispersion the dispersion can have a viscosity of 2000 cP or less, as measured at ambient conditions. In an additional embodiment, with a high solid contents of the dispersion being from 20 wt. % to 65 wt. % based on a total weight of the dispersion the dispersion can have a viscosity of 1000 cP or less, as measured at ambient conditions. In another embodiment, with a high solid contents of the dispersion being from 35 wt. % to 65 wt. % based on a total weight of the dispersion the dispersion can have a viscosity of 1000 cP or less, as measured at ambient conditions. In additional embodiments, the viscosity of the dispersion at the high solid content (e.g., from the upper to the lower limit as provided herein) can advantageously have a viscosity of 800 cP or less, and in various embodiments the dispersion can advantageously have a viscosity of 600 cP or less, or even a viscosity of 400 cP or less as measured at ambient conditions. In one or more embodiments, the dispersion of the present disclosure may also have the high solid content provided herein with a viscosity of greater than 1000 cP, or greater than 2000 cP, as measured at ambient conditions (e.g., a value of at least 10,000 cP as measured at ambient conditions).

Embodiments of the present disclosure are also able to maintain both the high solid content and the low viscosity at room temperature (25° C.) for various time intervals. For example, the dispersion of the present disclosure can maintain a viscosity of less than 10,000 cP with a high solid content of 20 wt. % to 65 wt. % of the starch particles based on the total weight of the dispersion after being at room temperature (25° C.) for 24 hours. In an additional example, the dispersion of the present disclosure can maintain a viscosity of less than 10,000 cP with a high solid content of 35 wt. % to 65 wt. % of the starch particles based on the total weight of the dispersion after being at room temperature (25° C.) for 24 hours.

In one or more embodiments, to achieve these viscosity values for the dispersion may require soluble starch present in the dispersion to be reduced from a starting molecular weight to an ending molecular weight that is less than the starting molecular weight. In one or more embodiments, soluble starch present in the dispersion of the starch particles can be either produced and/or released during the heating and/or shearing of the feed starch. In one or more embodiments, the soluble starch includes small fragments of the feed starch, relative the starch particles, which can significantly contribute to the viscosity of the dispersion. Reducing the soluble starch from the starting molecular weight to an ending molecular weight less than the starting molecular weight is helpful in reducing the viscosity of the dispersion by reducing the soluble starch into smaller fragments. Examples of suitable approaches to reducing the soluble starch from the starting molecular weight to the ending molecular weight less than the starting molecular weight include, but are not limited to, use of chemical modifications for example acid or alkali hydrolysis, acid reduction, oxidative reduction, physical/mechanical degradation (e.g., via the thermomechanical energy input of the processing equipment), and/or enzymatic reduction and/or microorganisms (such as bacteria, fungi, archaea, algae, and/or protests) to reduce molecular weight the soluble starch.

In one or more embodiments, reducing the soluble starch includes enzymatically reducing the soluble starch from the starting molecular weight to an ending molecular weight less than the starting molecular weight. The use of an enzyme in the present disclosure is helpful in reducing the viscosity of the dispersion by cleaving and/or enzymatically reducing the soluble starch into smaller fragments. In one or more embodiments, reducing/cleaving the soluble starch into these smaller fragments helps to improve the viscosity of the dispersion (e.g., helps to lower the viscosity) relative to not using the enzyme.

In one or more embodiments, the enzyme can be used during the process of preparing the dispersion of starch particles in the aqueous liquid. In one or more embodiments, the enzyme can be a soluble and/or it can be an immobilized enzyme. In one or more embodiments, the enzyme can be included in the rotor stator mixer with the feed starch and the aqueous liquid, where it can act on soluble starch as it is either produced and/or released from the feed starch as it absorbs the aqueous liquid, swells and/or is sheared into the starch particles. In one or more embodiments, the soluble starch as it is produced and/or released can have a starting molecular weight. The enzyme enzymatically reduces the soluble starch from the starting molecular weight to an ending molecular weight that is less than the starting molecular weight. In other words, the enzyme present in the rotor stator mixer can cleave the soluble starch into smaller fragments that have less of an impact on the viscosity of the dispersion.

In one or more embodiments, the enzyme selected for modifying the viscosity of the dispersion will depend on the compositions of the feed starch used in forming the dispersion. Given that the feed starch is based primarily on polysaccharide chemistries, enzymes capable of modifying the size (e.g., cleaving) carbohydrates will likely be most useful, and are known in the art. In one or more embodiments, the concentration of an enzyme useful in the present disclosure may be far lower than would be understood and/or recommended from the art. For example, it is believed that useful enzyme concentrations for the present disclosure can be 10 to 1000 times lower than what is suggested for starch modification by the enzyme manufactures. This can result in enzyme concentrations in the dispersion, for example, being 0.005 weight percent to 0.0001 weight percent relative the total weight of the dispersion (e.g. for waxy corn). As appreciated, the exact enzyme concentration suitable for modifying the viscosity of the dispersion can be dependent upon the temperature, the enzyme activity, the feed starch and/or the conditions under which the viscosity modification are taking place.

In one or more embodiments, the enzyme can be used at a temperature and at a duration that is sufficient to achieve the desired viscosity for the dispersion. In one or more embodiments, once the desired viscosity has been achieved, the enzyme can be "deactivated." In one or more embodiments, the enzyme may be deactivated by removal of a component needed to activate the enzyme. For example, enzymes may require the use of a particular salt at a particular concentration to allow the enzyme to function. Removal of the salt would, therefore, result in the deactivation of the enzyme. For example, the removal of calcium ions by chelation (e.g., the use of a chelating agent) may be sufficient to deactivate an enzyme that is used to cleave the soluble starch present in the dispersion of the present disclosure.

In one or more embodiments, the feed starch can be sheared into the starch particles of the dispersion in the absence of a cross-linker (e.g., without the use of cross linking chemistry). In one or more embodiments, shearing the feed starch into the starch particles of the dispersion can be conducted in the absence of a surfactant. In one or more embodiments, the use of one or more of a cross-linker and/or a surfactant is, however, possible with embodiments of the present disclosure. In one or more embodiments, the use of a cross-linker in preparing the dispersion of the present disclosure may help to change the molecular weight of the starch particle, relative not having used the cross-linker. Such changes to at least a portion of the molecular weight values of the starch particles of the present disclosure may provide for wet strength advantages derived from the dispersion in the application of paper coating formulations. It is appreciated that such cross-linkers could interact with the starch particles through hydrogen bonding, covalent bonding, or a combination of both.

In one or more embodiments, a variety of rotor stator mixers may be used according to the present disclosure. Examples of such rotor stator mixers include, but are limited to, batch high shear mixers, inline high shear mixers, ultra high shear inline mixers, and grinding mills (e.g., a Kady Mill), among others discussed herein. In one or more embodiments, the rotor stator mixer can be operated as part of a continuous process, a semi-continuous process and/or a batch process.

By way of example, a dispersion of starch particles in the aqueous liquid as described herein can be prepared in a continuous fashion in the following manner. In a stirred tank, the feed starch can be added to the aqueous liquid to create a slurry having, as provided herein, a lower limit to an upper limit of the amount of aqueous liquid introduced with the feed starch into the rotor stator mixer (e.g., from 40 wt. % to 60 wt. %, based on the weight of the aqueous liquid and the feed starch). In some cases, the rotor/stator mixer can be equipped with a powder feeding attachment which can allow the feed starch and the aqueous liquid to both be fed into the rotor/stator mixer in a continuous fashion. The ratio of flowrates of the two streams can be set to achieve a slurry having the desired amount of aqueous liquid introduced with the feed starch into the rotor stator mixer (e.g., from 40 wt. % to 60 wt. %, based on the weight of the aqueous liquid and the feed starch).

The slurry of the feed starch and the aqueous liquid can be pumped into a rotor/stator mixer, such that it passes through the mixer in a single pass. The temperature and flowrate of the slurry as well as the temperature of the jacket of the rotor/stator mixer can be maintained so the temperature of the slurry is from the gelation temperature to below the solubilization temperature of the feed starch, as discussed herein. Shear force, in ranges provided herein, can then be applied to the feed starch in its swollen state so as to create the dispersion of starch particles, as discussed herein. In some cases a solution of an enzyme as discussed herein (for example water containing 0.15 wt. % enzyme and 0.19 wt. % calcium chloride) can be added continuously into dispersion in the rotor/stator mixer through a separate injection port. In some cases, a second rotor/stator mixer (equipped with a second mixer jacket for cooling) can be placed in line after the rotor/stator mixer to provide additional shear to further reduce the size of the starch particles in the dispersion, if desired. Rotor speed, rotor design, rotor operational pattern(s), flowrate of the components (e.g., feed starch and aqueous liquid), pressure and temperature are examples of variables in the continuous production of the dispersion of starch particles in the aqueous liquid according to the present disclosure. Selection and values for such variables can be dependent upon, among other things, the feed starch, the aqueous liquid and/or any optional additives selected in preparing the dispersion of the present disclosure.

In one or more embodiments, optional additives can also be used in the process of the present disclosure. For example, anionic and ionic stabilizers might be added to the dispersion during the shearing process to reduce particle agglomeration during drying. In an additional example, a plasticizer may be present in addition to the feed starch and the aqueous liquid. Examples of plasticizers include a polyol (e.g. ethylene glycol, propylene glycol, polyglycols, glycerol, sucrose, maltose, maltodextrins, and sugar alcohols such as sorbitol), urea, sodium lactate, amino acids, or citric acid esters, at a level of from 5 to 40% by weight based on the dry weight of the feed starch. However, water can already act as a plasticizer. The total amount of plasticizers (i.e. water and additional plasticizer) can range from 5% and 65% by weight based on the dry weight of the feed starch. A lubricant, such as lecithin, other phospholipids or monoglycerides, may also be present at a level of 0.5% to 2.5% by weight based on the dry weight of the feed starch.

In one or more embodiments, optional additives can also be added to the dispersions of the present disclosure. Such additives include, but are not limited to, biocides, anti-microbial additives, a base and/or an acid for pH adjustment, pigments, flavor or fragrance enhancers, inorganic and/or organic inert fillers or pigments, and combinations thereof.

In one embodiment, the dispersion of the present disclosure is ready to use out of the rotor stator mixer as is. This advantageously reduces the expense associated with drying steps required by some prior art processes to concentrate the material into a powder form. It is, however, possible to at least partially, i.e. less than 90 percent, substantially, i.e. at least 90 percent, and/or fully, i.e. at least 98 percent, remove the aqueous liquid from the starch particles of the dispersion to concentrate the solid content of the dispersion or to form a dry redispersible powder of the starch particles for redispersion later. As provided herein, at least partially, i.e. less than 90 percent, substantially, i.e. at least 90 percent, and/or fully, i.e. at least 98 percent, removing the aqueous liquid from the starch particles of the dispersion can form a dry redispersible powder having an average particle size diameter of no larger than 20 µm, for example, no larger than 10 µm; in the alternative, no larger than 5 µm; in the alternative, no larger than 4 µm; in the alternative, no larger than 2 µm. The dry redispersible power particles may agglomerate during the drying steps to form larger particles than the starch particles in the dispersion. The agglomerated particles may be dispersed into a dispersion having an average particle size diameter of no larger than 2 µm; for example, from an average particle size diameter of no larger than 1 µm or an average particle size diameter of 10 to 200 nanometers.

Various means for reducing the aqueous liquid content of dispersions and/or for drying the dispersion are known to those skilled in the art. Examples of these means include air drying, forced air drying, spray drying, pressurized filtration and centrifugation, among others. In one or more embodiments, the dry powder of the starch particles can be further milled to break the particles and/or particle aggregates into the desired size. The dry powder of the starch particles of the present disclosure can then be resuspended in a dispersion at a desired time. In one or more embodiments, it may also be possible to add additional water to the dispersion to alter the solid content to a desired level.

In one or more embodiments, dry powders of the starch particles can also be blended with other powders, compounds and/or dispersion prior to or at the time of resuspension. Examples of such powders, compounds and/or dispersions include, but are not limited to, latexes, latex and non-latex binders, dispersions, pigments, among others useful for film coating, adhesive and/or binder systems, as are provided herein.

The starch particles of the present disclosure can also be blended with one or more of the following additional components. Such additional components can be blended with the starch particles in the dispersion or can be blended with a dry powder of the starch particles. In one or more embodiments, the additional component can include one or more binder compositions such as acrylic latex, vinyl acrylic latex, styrene acrylic latex, styrene butadiene latex, vinyl acetate ethylene latex, modified cellulosic binders such as methylcellulose, hydroxypropyl cellulose, and combinations thereof; optionally one or more fillers; optionally one or more additives; optionally one or more pigments, e.g. titanium dioxide, mica, calcium carbonate, silica, zinc oxide, milled glass, aluminum trihydrate, talc, antimony trioxide, fly ash, and clay; optionally one or more co-solvents, e.g. glycols, glycol ether, 2,2,4-trimethyl-1,3-pentanediol monoisobutyrate, alcohols, mineral spirits, and benzoate esters; optionally one or more dispersants, e.g. aminoalcohols, and polycarboxylates; optionally one or more surfactants; optionally one or more defoamers; optionally one or more preservatives, e.g. biocides, mildewcides, fungicides, algaecides, and combinations thereof; optionally one or more thickeners, e.g. cellulosic based thickeners such as hydroxyethyl cellulose, hydrophobically modified alkali soluble emulsions (HASE thickeners such as UCAR® POLYPHOBE TR-116 from The Dow Chemical Company) and hydroobically modified ethoxylated urethane thickeners (HEUR); or optionally one or more additional neutralizing agents, e.g. hydroxides, amines, ammonia, and carbonates.

The additional components can also include, but are not limited to, polysaccharide derivatives, including cellulose derivatives. Examples of such polysaccharide derivatives include polysaccharide ethers and polysaccharide esters, cellulose ethers and esters, and water-soluble cellulose ethers. They can have one or more substituents such as of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. The substituents of the polysaccharides according to the present disclosure are not limited to these groups. Typical polysaccharide derivatives are guar derivatives, starch derivatives, chitin or chitosan derivatives, and cellulose derivatives, but the polysaccharide derivatives according to the disclosure are not limited to these.

Examples of cellulose derivatives can include, but are not limited to, hydroxyethyl cellulose (HEC), hydroxypropyl cellulose (HPC), ethyl hydroxyethyl cellulose (EHEC), carboxymethyl cellulose, carboxymethyl hydroxyethyl cellulose (CMHEC), hydroxypropyl hydroxyethyl cellulose (HPHEC), methyl cellulose (MC), methyl hydroxypropyl Cellulose (MHPC), methyl hydroxyethyl cellulose (MHEC), carboxymethyl cellulose (CMC), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CMSEC), hydrophobically modified sulfoethyl cellulose (hmSEC), hydrophobically modified hydroxyethyl sulfoethyl cellulose (hmHESEC), hydrophobically modified hydroxypropyl sulfoethyl cellulose (hmHPSEC) or hydrophobically modified hydroxyethyl hydroxypropyl sulfoethyl cellulose (hmHEHPSEC). Other suitable cellulose derivatives include cellulose ethers having a thermal flocculation point in water, such as, for example, methyl cellulose, methyl hydroxyethyl cellulose, methyl hydroxypropyl cellulose and hydroxypropyl cellulose.

Embodiments of the present disclosure may also employ a colorant as part of the dispersion. A variety of colors may be used. Examples include colors such as yellow, magenta, and cyan. As a black coloring agent, carbon black, and a coloring agent toned to black using the yellow/magenta/cyan coloring agents shown below may be used. Colorants, as used herein, include dyes, pigments, and predispersions, among others. These colorants may be used singly, in a mixture, or as a solid solution. In various embodiments, pigments may be provided in the form of raw pigments, treated pigments, pre-milled pigments, pigment powders, pigment presscakes, pigment masterbatches, recycled pigment, and solid or liquid pigment predispersions. As used herein, a raw pigment is a pigment particle that has had no wet treatments applied to its surface, such as to deposit various coatings on the surface. Raw pigment and treated pigment are further discussed in PCT Publication No. WO 2005/095277 and U.S. Patent Application Publication No. 2006/0078485, the relevant portions of which are incorporated herein by reference. In contrast, a treated pigment may have undergone wet treatment, such as to provide metal oxide coatings on the particle surfaces. Examples of metal oxide coatings include alumina, silica, and zirconia. Recycled pigment may also be used as the starting pigment particles, where recycled pigment is pigment after wet treatment of insufficient quality to be sold as coated pigment.

Exemplary colorant particles include, but are not limited to, pigments such as yellow coloring agent, compounds typified by a condensed azo compound, an isoindolynone compound, an anthraquinone compound, an azometal complex methine compound, and an allylamide compound as pigments may be used. As a magenta coloring agent, a condensed azo compound, a diketopyrrolopyrrole compound, anthraquinone, a quinacridone compound, a base dye lake compound, a naphthol compound, a benzimidazolone compound, a thioindigo compound, and a perylene compound may be used. As a cyan coloring agent, a copper phthalocyanine compound and its derivative, an anthraquinone compound, a base dye lake compound, and the like may be used.

Dispersions of the present disclosure may be used, for example, in different coating applications such as architectural coating applications, automotive coating applications, paper coating applications, paper sizing applications, seed coating applications, conductive coatings and industrial coating applications, adhesives applications, binder applications, sealant applications, foam applications, toner applications, immediate release coating applications, and controlled released coating applications, among others.

The dispersion may be employed in existing applications where starch and/or latex are used. For example, the dispersion can be used in a paper coating composition. Paper coating compositions can be prepared substituting wholly or partially the starch dispersion material for other conventional binders such as latex and conventional coating starches.

Surprisingly, a significant advantage of the dispersion of the present disclosure is that it can remain shelf-stable at 25° C. for a time of at least 52 weeks.

In one or more embodiments, the dispersion of the present disclosure can be used in a variety of applications. Such applications include, but are not limited to, coating compositions, adhesives (e.g., tapes, labels, book bindings, etc.), pharmaceuticals (e.g., as an extender in tablet coatings), as a binder and/or filler in wet laminations and/or wood composites, fiberglass shingle mats, and/or polyester spun-bond applications like roofing and carpet backing. They could also be used in paper coatings compositions, carpet binding applications, mastics, joint compounds, and/or cements.

Suitable substrates for the dispersion of the present disclosure include, but are not limited to, cellulosic based materials, such a paper, paper board, and/or cardboard, metal based materials, polymeric based materials (synthetic and/or natural), and mineral based materials (e.g., concrete), among others. The dispersions of the present disclosure may also be used in existing starch applications, existing synthetic latex applications, coating applications, latex formulations where some of the latex can be replaced by the dispersion of the present disclosure.

The dispersions according to the present invention may be applied to one or more surface of a suitable substrate via methods known to a person of ordinary skill in the art such as spraying, printing, roll coating, jet coating, film coating, puddle coating, curtain coating, and/or dipping, and subsequently at least a portion of aqueous liquid may be removed thereby forming a coating layer, for example a film, associated with one or more surfaces of the substrate.

Additional subject matter included in this application includes, but is not limited to, the following: A dispersion of starch particles prepared by the process recited herein. A binder composition comprising a dispersion of starch particles prepared by the process recited herein. An adhesive composition comprising a dispersion of starch particles prepared by the process recited herein. The coating composition as recited herein, where the coating composition is applied to one or more surfaces of a substrate. The coating composition as recited herein, where the coating composition is a film forming composition. The coating composition as recited herein, where the portion of the aqueous liquid is removed via drying, centrifuge, freeze drying, filtration or absorption.

EXAMPLES

The following examples are given to illustrate embodiments of the present disclosure and should not be construed as limiting its scope. All parts and percentages are by weight unless otherwise indicated.

Test Methods

Sheet Gloss

Sheet gloss is measured using a Technidyne T-480 instrument at an incident angle of 75°, available from Technidyne Corporation. Sheet gloss is a property that describes coated paper's shiny or lustrous appearance and is a measurement of a sheet's surface reflectivity.

Sheet Brightness (GE Brightness)

Sheet brightness is measured using a Technidyne Brightimeter Micro S-5 and the Colortouch PC instrument available from Technidyne Corporation. Brightness is a numerical value of the reflectance factor of a sample with respect to blue light. The instrument has a light source that shines onto a piece of paper at 45 degrees with receiving optics that view that same spot from zero degrees, perpendicular to the sample.

Brookfield Viscosity

The viscosity is measured using a Brookfield RVT viscometer (available from Brookfield Engineering Laboratories, Inc., Stoughton, Mass., USA). For viscosity determination, a sample is poured into a suitably large container to avoid edge effects between the wall and the spindle. The viscosity is measured at around 25° C. with a variety of spindle sizes and rotation speeds depending on the characteristics of the sample being measured. The values reported in Tables 1 and 2 were obtained with a number 3 spindle and 100-rpm condition.

Materials

The following materials are used in the examples.

Starch A: waxy corn starch (Douglas Waxy Pearl Starch available from Penford, Cedar Rapids, Iowa), dry powder containing about 11% moisture.

Starch B: dent corn starch (Pearl Starch available from Penford, Cedar Rapids, Iowa), dry powder containing about 11% moisture.

Starch C: native waxy corn starch (Merizet 300 available from Tate and Lyle, Koog, Netherlands), dry powder containing about 11% moisture.

Calcium chloride: 10 weight percent solution of calcium chloride in water (Calcium chloride from Fischer Scientific, Fair Lawn, N.J.).

Crosslinker: Glyoxal (EKA RC 5550 available from Eka Chemicals Inc., Marietta, Ga., USA).

Insolulubilizer: Surface strength improver (Cartabond TSI (42%) available from Clariant, Muttenz, Switzerland).

Bleach: 2.5 weight percent sodium hypochlorite solution in water (household bleach available from Clorox, Corp.).

Enzyme: enzyme preparation (BAN 480L available from Novozymes A/S, Bagsvaerd, Denmark).

Chelating Agent: chelating preparation in water (VERSENOL 120 available from Dow Chemical, Midland, Mich.).

Carbonate: dispersion of calcium carbonate with particle size of 90%<2 μm in water (Hydrocarb® 90 available from Pluess-Stauffer, Oftringen, Switzerland), 77% solids.

Clay: dispersion of No. 1 high brightness kaolin clay with particle size of 90-96%<2 μm in water (Hydrafine® 90 available from KaMin Performance Materials, Macon, Ga., USA), 71% solids.

Latex: carboxylated styrene-butadiene latex (CP 638NA available from The Dow Chemical Company, Midland, Mich., USA), 50% solids in water.

Caustic: 20% sodium hydroxide solution (Fisher Scientific, Fair Lawn, N.J.).

Water: De-ionized water.

Paper: An 88 gram/square meter wood-free base paper from Appleton Coated, Appleton, Wis.

Equipment

Lab Kady-Mill mixer serial number L-744 from Kady International of Scarborough, Mass. with Stator #1 mixing head and 2.24 kW motor.

GAW Agitator, model RW 60 S-VST Rotor Stator from GAW Pidlner-Steinburg GmbH, Graz, Austria. with 50 hp motor drive and a 473 liter container.

Example 1

Prepare the dispersion by first measuring an amount of Starch A and deionized water, both at room temperature (25° C.), to make a mixture having a 50 weight percent solids content. Place a sufficient amount of the mixture into the mixing bowl of the Lab Kady-Mill mixer to adequately cover the rotor stator as to prevent splashing (e.g., where a sufficient amount of the mixture for the present example is 750 grams of Starch A and 665 grams of deionized water). Set the motor drive speed setting of the Lab Kady-Mill mixer to number "10" (scale of 1 to 10) and mix the feed starch and water mixture having the 50 weight percent solids content for 5.5 minutes until the resulting dispersion does not circulate in the mixing bowl under agitation. Reduce the speed of the motor drive speed setting to number "4" and add water to the dispersion to bring the solids content to 25 weight percent. Mix the dispersion at the motor drive speed setting number "4" for 5 additional minutes. The result is a stable dispersion of starch particles in the aqueous liquid, according to the present disclosure, that does not gel after storage at room temperature (25° C.) for 24 hours.

Example 2

Prepare the dispersion by first measuring an amount of Starch A and deionized water, both at room temperature (25° C.), to make a mixture having a 50 weight percent solids content. Add 1 part cross-linker based on 100 parts of dry Starch A to the mixture. Place a sufficient amount of the mixture into the mixing bowl of the Lab Kady-Mill mixer to adequately cover the rotor stator as to prevent splashing (e.g., where a sufficient amount of the mixture for the present example is 750 grams of Starch A and 665 grams of deionized water). Set the motor drive speed setting of the Lab Kady-Mill mixer to number "10" (scale of 1 to 10) and mix the feed starch and water mixture having the 50 weight percent solids content for 5.5 minutes until the resulting dispersion does not circulate in the mixing bowl under agitation. Reduce the speed of the motor drive speed setting to number "4" and add water to the dispersion to bring the solids content to 25 weight percent. Mix the dispersion at the motor drive speed setting number "4" for 5 additional minutes. The result is a stable dispersion of starch particles in the aqueous liquid, according to the present disclosure, that does not gel after storage at room temperature (25° C.) for 24 hours.

Example 3

Prepare the dispersion by first measuring an amount of Starch B and deionized water, both at room temperature (25° C.), to make a mixture having a 50 weight percent solids content. Place a sufficient amount of the mixture into the mixing bowl of the Lab Kady-Mill mixer to adequately cover the rotor stator as to prevent splashing (e.g., where a sufficient amount of the mixture for the present example is 750 grams of Starch B and 665 grams of deionized water). Set the motor drive speed setting of the Lab Kady-Mill mixer to number "10" (scale of 1 to 10) and mix the feed starch and water mixture having the 50 weight percent solids content for 5.5 minutes until the resulting dispersion does not circulate in the mixing bowl under agitation. Reduce the speed of the motor drive speed setting to number "4" and add water to the dispersion to bring the solids content to 25 weight percent. Mix the dispersion at the motor drive speed setting number "4" for 5 additional minutes. The result is a stable dispersion of starch particles in the aqueous liquid, according to the present disclosure, that does not gel after storage at room temperature (25° C.) for 24 hours.

Example 4

Prepare the dispersion by first measuring an amount of Starch B and deionized water, both at room temperature (25° C.), to make a mixture having a 50 weight percent solids content. Add 1 part cross-linker based on 100 parts of dry Starch B to the mixture. Place a sufficient amount of the mixture into the mixing bowl of the Lab Kady-Mill mixer to adequately cover the rotor stator as to prevent splashing (e.g., where a sufficient amount of the mixture for the present example is 750 grams of Starch B and 665 grams of deionized water). Set the motor drive speed setting of the Lab Kady-Mill mixer to number "10" (scale of 1 to 10) and mix the feed starch and water mixture having the 50 weight percent solids content for 5.5 minutes until the resulting dispersion does not circulate in the mixing bowl under agitation. Reduce the speed of the motor drive speed setting to number "4" and add water to the dispersion to bring the solids content to 25 weight percent. Mix the dispersion at the motor drive speed setting number "4" for 5 additional minutes. The result is a stable dispersion of starch particles in the aqueous liquid, according to the present disclosure, that does not gel after storage at room temperature (25° C.) for 24 hours.

Paper Coating Compositions Prepared with the Dispersions of Examples 1 Through 4

For each of the dispersions of Examples 1 through 4 prepare a paper coating composition based on 100 parts total pigment on a dry basis. Specifically, prepare a pigment slip using 60 parts by dry weight of the Carbonate and 40 parts by dry weight of the Clay, as provided hereinabove. Then add 5 parts by dry weight Latex and 9 parts by dry weight of the dispersion as provided in Table 1. Finally, add 0.1 parts by dry weight of the insolubilizer to the paper coating composition. Adjust the pH to 8.5 with 20% aqueous sodium hydroxide and adjust the solids content with water to 61.0%.

Prepare coated paper using the paper coating compositions in the following process. Utilize a laboratory bench blade coater (manufactured by Enz Technik A G, Giswil, Switzerland) to apply the paper coating compositions to the paper. Set the blade metering pressure to apply 8 lbs/3300 sq ft and dry the resulting paper coating composition using infrared and air flotation drying to reach a target moisture of 4.5%. Cut the resulting paper samples into sheets and then lab calendar using a Beloit Wheeler Laboratory Calendar Model 753 (manufactured by Beloit Manhattan, Otsego, Mich., USA) using 3 passes through a single nip at 65 deg ° C. and a pressure loading equivalent to 800 pounds per linear inch (pli). The properties of the coated paper are given in Table 1.

TABLE 1

Properties of Paper coated with the Paper Coating Compositions that include the Dispersion of Examples 1 through 4

| Dispersion used in the Paper Coating Composition | Brookfield Viscosity [cP] of Paper Coating Composition | Sheet Gloss (75 deg CMD*) of the Paper coated with the Paper Coating Composition | GE Brightness of the Paper coated with the Paper Coating Composition |
|---|---|---|---|
| Example 1 | 206 | 67.8 | 86.8 |
| Example 2 | 284 | 64.0 | 86.9 |
| Example 3 | 912 | 63.8 | 86.7 |
| Example 4 | 710 | 65.7 | 86.6 |

*Cross Machine Direction

Example 5

Prepare the dispersion by first measuring an amount of Starch C and water, both at room temperature (25° C.), to make a mixture having a 45 weight percent solids content. Place 113.4 kg of Starch C and 126.6 kg of water in the tank of the GAW Mixer body. Set the speed setting of the GAW Mixer to 1800 rpm on the motor drive speed control and mix the mixture having the 45 weight percent solids content for 30 minutes until the resulting dispersion reaches a temperature of 65.5° C. Add 200 parts per million based on dry weight calcium chloride via a 10% solution. Add 0.00005 parts of the enzyme, based on 100 parts of dry Starch C, to the dispersion and mix for an additional 30 minutes. Reduce the speed setting of the GAW Mixer to 600 rpm on the motor drive speed control. Add the chelating agent at 2000 parts per million and mix the dispersion for an additional 10 minutes.

The result is a stable dispersion of starch particles in the aqueous liquid that does not gel after storage at room temperature (25° C.) for 24 hours.

Comparative Example A

Prepare the dispersion by first measuring an amount of Starch B and deionized water, both at room temperature (25° C.), to make a mixture having a 40 weight percent solids content. Place a sufficient amount of the mixture into the mixing bowl of the Lab Kady-Mill mixer to adequately cover the rotor stator as to prevent splashing (e.g., where a sufficient amount of the mixture for the present example is 750 grams of Starch B and 998.9 grams of deionized water). Set the motor drive speed setting of the Lab Kady-Mill mixer to number "10" (scale of 1 to 10) and mix the feed starch and water mixture having the 40 weight percent solids content for 5.5 minutes until the resulting dispersion does not circulate in the mixing bowl under agitation. Reduce the speed of the motor drive speed setting to number "4" and add water to the dispersion to bring the solids content to 25 weight percent. Mix the dispersion at the motor drive speed setting number "4" for 5 additional minutes.

The result is a dispersion of starch in water that gels after room temperature storage (25° C.) after 24 hours. The material will not pour from the container, and it is not suitable for a component in a coating formulation.

Comparative Example A illustrates the need to have a higher weight percent solids content during the shearing process (as compared to the final solids content of the resulting dispersion, which was in both cases 25 weight percent solids content). In Comparative Example A there was a 40 weight percent solids content during the shearing process, as compared to a 50 weight percent solids content for Example 3. So, in Comparative Example A there is approximately 20 percent less solids content, as compared to Example 3, in the mixture during the shearing process which allows for fewer starch particles to pass through the shearing points in the mixer. In other words, for Example 3 there is approximately 25 percent greater solids content, as compared to the Comparative Example A, in the mixture during the shearing process. This higher solids content during the shearing process is believed to be important in achieving the stable dispersion of starch particles of the appropriate average particle size diameter, as discussed herein.

Table 2, below, provides a summary of Brookfield Viscosity Values for the Dispersions of Examples 1-5, and Comparative Example A.

| Example | Weight Percent Solids Content During Shear | Brookfield Viscosity [cP] - initial | Brookfield Viscosity [cP] - after 3 days | Brookfield Viscosity [cP] - after 10 days |
|---|---|---|---|---|
| Example 5 | 45 | 1300 | Not gelled | Not gelled |
| Comparative Example A | 40 | 363 | Not measureable - Sample gelled | Not measureable - Sample gelled |
| Example 1 | 50 | 66 | 94 | 83 |
| Example 2 | 50 | 128 | 120 | 125 |
| Example 3 | 50 | 141 | 683 | 407 |
| Example 4 | 50 | 203 | 395 | 428 |

What is claimed is:

1. A process for preparing a dispersion of starch particles in an aqueous liquid, the process comprising:
    heating a feed starch and the aqueous liquid to a temperature ranging from a gelation temperature to less than a solubilization temperature for the feed starch; and
    shearing the feed starch into starch particles having an average particle size diameter of no larger than 2 micrometers in the absence of a cross-linker at the temperature ranging from the gelation temperature to less than the solubilization temperature of the feed starch.

2. The process of claim 1, including crosslinking the starch particles with a cross-linker after the shearing step.

3. The process of claim 1, where shearing the feed starch into starch particles includes forming the dispersion having 20 to 65 weight percent of the starch particles based on a total weight of the dispersion.

4. The process of claim 1, where shearing the feed starch into starch particles includes using a rotor stator to shear the feed starch into starch particles.

5. The process of claim 1, where shearing the feed starch into starch particles is conducted in the absence of a surfactant.

6. The process of claim 1, where shearing the feed starch produces soluble starch having a starting molecular weight; and
    reducing the soluble starch from the starting molecular weight to an ending molecular weight less than the starting molecular weight.

7. The process of claim 6, where reducing the soluble starch includes enzymatically reducing the soluble starch from the starting molecular weight to an ending molecular weight less than the starting molecular weight.

8. The process of claim 1, where a viscosity of the dispersion having 20 to 65 weight percent of the starch particles based on a total weight of the dispersion is less than 10,000 cP after being at 25° C. for 24 hours.

9. The process of claim 1, including at least partially removing the aqueous liquid from the starch particles of the dispersion.

10. The process of claim 1, including at least partially removing the aqueous liquid from the starch particles of the dispersion thereby forming a dry redispersible powder.

11. The process of claim 1, including at least partially removing the aqueous liquid from the starch particles of the dispersion thereby forming a dry redispersible powder having an average particle size diameter of no larger than 2 micrometer.

12. A coating composition comprising a dispersion of starch particles prepared by the process of claim 1.

13. The coating composition of claim 12, where the coating composition is a paper coating composition.

14. The coating composition of claim 12, where the coating composition is applied to one or more surfaces of a substrate, and wherein a portion of the aqueous liquid is removed thereby forming a coating layer associated with one or more surfaces of the substrate.

* * * * *